United States Patent
Wen et al.

(10) Patent No.: US 10,052,239 B1
(45) Date of Patent: Aug. 21, 2018

(54) DIAPER PREDICTION AND CORRECTION SYSTEM AND METHOD

(71) Applicant: Cvilux Corporation, New Taipei (TW)

(72) Inventors: Ming-Hui Wen, Taichung (TW);
Wei-Nan Liu, Taipei (TW); Sean Jeremy Wilson, Columbia, MD (US)

(73) Assignee: CVILUX CORPORATION, New Taipei (TW)

( * ) Notice: Subject to any disclaimer, the term of this patent is extended or adjusted under 35 U.S.C. 154(b) by 0 days.

(21) Appl. No.: 15/896,244

(22) Filed: Feb. 14, 2018

(30) Foreign Application Priority Data

Sep. 18, 2017 (TW) .............................. 106131968 A

(51) Int. Cl.
| | |
|---|---|
| *A61F 13/42* | (2006.01) |
| *H04W 4/38* | (2018.01) |
| *G01N 27/04* | (2006.01) |
| *G08B 21/20* | (2006.01) |

(52) U.S. Cl.
CPC ........... *A61F 13/42* (2013.01); *G01N 27/048* (2013.01); *G08B 21/20* (2013.01); *H04W 4/38* (2018.02)

(58) Field of Classification Search
None
See application file for complete search history.

(56) References Cited

U.S. PATENT DOCUMENTS

| | | | |
|---|---|---|---|
| 2005/0033250 A1* | 2/2005 | Collette | A61F 13/42 604/361 |
| 2012/0268278 A1* | 10/2012 | Lewis | A61F 13/42 340/573.5 |
| 2013/0254141 A1* | 9/2013 | Barda | A61F 13/42 706/12 |
| 2014/0327546 A1* | 11/2014 | Carney | A61F 13/42 340/573.5 |
| 2015/0330958 A1* | 11/2015 | Carney | A61F 13/42 73/23.34 |

FOREIGN PATENT DOCUMENTS

| | | | |
|---|---|---|---|
| CN | 104127277 B | 9/2015 | |
| WO | WO 2013095231 A1 * | 6/2013 | G06F 19/3418 |

* cited by examiner

*Primary Examiner* — Brian Zimmerman
*Assistant Examiner* — Sara Samson
(74) *Attorney, Agent, or Firm* — McClure, Qualey & Rodack, LLP

(57) ABSTRACT

The present disclosure provides diaper prediction and correction system and method. This system includes a diaper sensor, a server and a mobile device. The server is configured to store crowdsourcing data including a plurality of sensing criteria corresponding to a plurality of geographic regions, different genders, a plurality of ages, a plurality of diaper data. The mobile device is configured to execute a mobile application to pair with the diaper sensor and to transmit a location information, a wearer's sex and age, and a brand or a model of a diaper to the server, so that the server selects a corresponding sensing criterion from the sensing criteria and returns the corresponding sensing criterion to the mobile device, and the mobile device is based on the corresponding sensing criterion to determine whether a diaper sensing signal from the diaper sensor reflect that the diaper needs to be replaced.

8 Claims, 2 Drawing Sheets

DIAPER PREDICTION AND CORRECTION SYSTEM AND METHOD

RELATED APPLICATIONS

This application claims priority to Taiwan Patent Application No. 106131968, filed Sep. 18, 2017, the entirety of which is herein incorporated by reference.

BACKGROUND

Field of Invention

The present invention relates to diaper care systems and methods for multiple users.

Description of Related Art

A diaper or a nappy is a type of underwear that allows the wearer to defecate or urinate without the use of a toilet, by absorbing or containing waste products to prevent soiling of outer clothing or the external environment. Failure to change a diaper on a sufficiently regular basis can result in skin problems around the area covered by the diaper. Diapers using a very strong polymer as an absorber, and some can absorb up to 50 times its own weight of water.

However, dependents (e.g., parents of infants) are often unsure when THE infants need to change diapers after urination.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one or more various aspects, the present disclosure is directed to diaper prediction and correction systems and methods.

An embodiment of the present disclosure is related to a diaper prediction and correction system including a diaper sensor, a server and a mobile device. The server is configured to store crowdsourcing data including a plurality of sensing criteria corresponding to a plurality of geographic regions, different genders, a plurality of ages, a plurality of diaper data. The mobile device is configured to execute a mobile application to pair with the diaper sensor and to transmit a location information, a wearer's sex and age, and a brand or a model of a diaper to the server, so that the server selects a corresponding sensing criterion from the sensing criteria and returns the corresponding sensing criterion to the mobile device, and the mobile device is based on the corresponding sensing criterion to determine whether a diaper sensing signal from the diaper sensor reflect that the diaper needs to be replaced.

In one embodiment, the sensing criteria in the crowdsourcing data correspond to relations among the geographical regions, the genders, the ages, the diaper data and a plurality of environmental parameters, and before the diaper attached to the diaper sensor is worn, the diaper sensor senses an environmental sensing signal, so that the mobile device sends transmit the location information, the wearer's sex and age, the brand or the model of diaper, and the environmental sensing signal to the server 150, so as to obtain the corresponding sensing criterion.

In one embodiment, after the mobile device executes a prompt action of replacement of the diaper, the mobile device receives user feedback information, adjusts the corresponding sensing criterion based on the user feedback information and uploads the user feedback information to the server, so that the server uses the user feedback information as a basis of updating the crowdsourcing data.

In one embodiment, the diaper sensor includes a wireless transmitter, a temperature sensor, a humidity sensor and a controller. The temperature sensor is configured to sense a temperature value. The humidity sensor is configured to sense a humidity value. The controller is configured to incorporate the temperature value and the humidity value into the diaper sensing signal so as to transmit the diaper sensing signal to the mobile device through the wireless transmitter, so that the mobile device determines whether the temperature value and the humidity value falls within a predetermined temperature range and a preset humidity range respectively, and the mobile device determines that the diaper which needs to be replaced when the temperature value and the humidity value falls within the predetermined temperature range and the preset humidity range respectively.

In one embodiment, another embodiment of the present disclosure is related to a diaper prediction and correction method including steps of: (A) using a server to store crowdsourcing data including a plurality of sensing criteria corresponding to a plurality of geographic regions, different genders, a plurality of ages, a plurality of diaper data; and (B) using a mobile device to execute a mobile application to pair with a diaper sensor and to transmit a location information, a wearer's sex and age, and a brand or a model of a diaper to the server, so that the server selects a corresponding sensing criterion from the sensing criteria and returns the corresponding sensing criterion to the mobile device, and the mobile device is based on the corresponding sensing criterion to determine whether a diaper sensing signal from the diaper sensor reflect that the diaper needs to be replaced.

In one embodiment, the sensing criteria in the crowdsourcing data correspond to relations among the geographical regions, the genders, the ages, the diaper data and a plurality of environmental parameters, and the step (B) further includes: before the diaper attached to the diaper sensor is worn, using the diaper sensor to sense an environmental sensing signal, so that the mobile device sends transmit the location information, the wearer's sex and age, the brand or the model of diaper, and the environmental sensing signal to the server, so as to obtain the corresponding sensing criterion.

In one embodiment, the diaper prediction and correction method further includes: after the mobile device executes a prompt action of replacement of the diaper, using the mobile device to receive user feedback information, adjust the corresponding sensing criterion based on the user feedback information and upload the user feedback information to the server, so that the server uses the user feedback information as a basis of updating the crowdsourcing data.

In one embodiment, the step (B) includes: using the diaper sensor to incorporate a temperature value and a humidity value of the diaper into the diaper sensing signal so as to transmit the diaper sensing signal to the mobile device, so that the mobile device determines whether the temperature value and the humidity value falls within a predetermined temperature range and a preset humidity range respectively, and the mobile device determines that the diaper which needs to be replaced when the temperature value and the humidity value falls within the predetermined temperature range and the preset humidity range respectively.

Technical advantages are generally achieved, by embodiments of the present invention. The present invention provides a set of mechanisms for the diaper sensor to quickly and easily establish a "customized predictive model" for wearers of different diaper brands, different breathable degrees, and different ages, in both hot and cold environments, so as to accurately determine when to change diapers.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
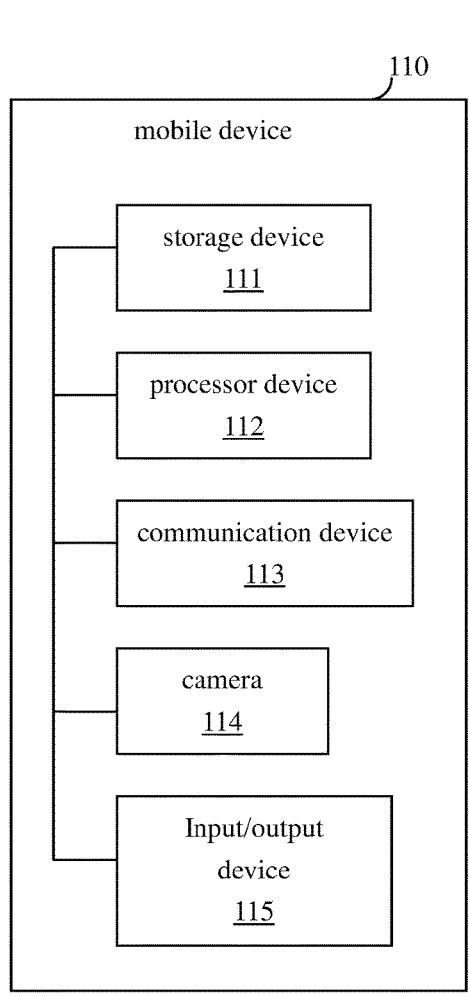
FIG. 1 is a block diagram of a diaper prediction and correction system according to some embodiments of the present disclosure.
Figure 1:
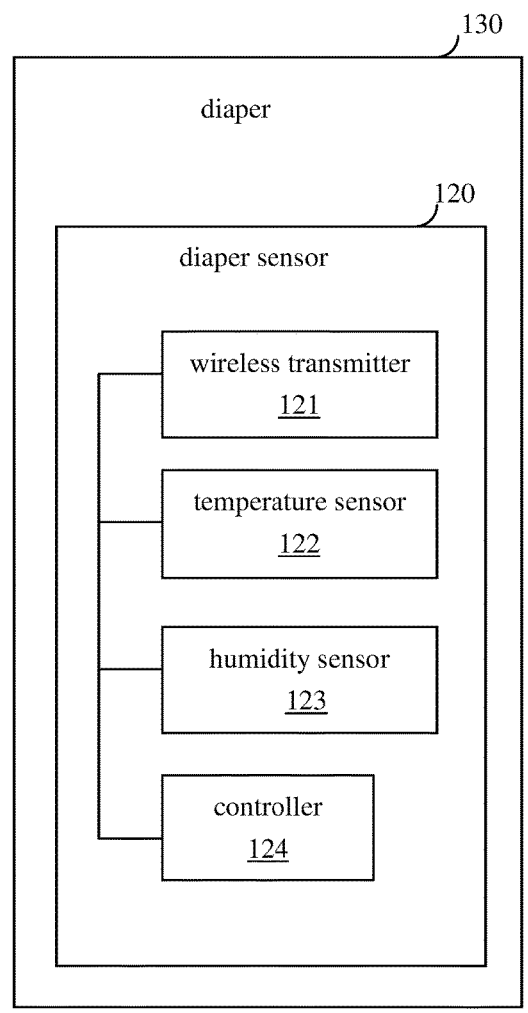
Figure 1:
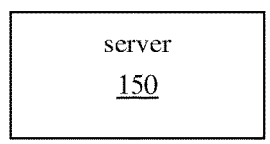

Reference will now be made in detail to the present embodiments of the invention, examples of which are illustrated in the accompanying drawings. Wherever possible, the same reference numbers are used in the drawings and the description to refer to the same or like parts.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a block diagram of a diaper prediction and correction system 100 according to some embodiments of the present disclosure. As shown in FIG. 1, the diaper care system 100 includes a mobile device 110, a server 150 and a diaper sensor 110. The mobile device 110 can wirelessly communicate with the diaper sensor 120. The mobile device 110 can perform the predictive calibration of the diaper sensor 120 through the server 150. The diaper sensor 120 are detachably attached to the diaper by means of a devil felt, a fastener, an adhesive, or the like, but the present invention is not limited thereto.

In FIG. 1, the mobile device 110 includes a storage device 111, a processor device 112, a communication device 113, a camera device 114, and an input/output device 115. The processor device 112 is electrically connected to the storage device 111, the communication device 113, the camera device 114, and the input/output device 115.

In practice, the mobile device 110 may be a mobile phone, a tablet or similar electronic device. The storage device 111 may be a hard disk or a flash memory. The processor device 112 may be a central processing unit or a micro-controller. The communication device 113 may include a Bluetooth module, a mobile network module, an area wireless network module, etc. The camera device 114 may be a camera hardware module. The input/output device 115 may be a touch screen, a separate screen with a button, a wearable device or a voice device, so as to perform operations such as chat-bot, voice-bot or the like.

In use, the storage device 111 is configured to store a mobile application (e.g., software program), the processor device 112 is configured to execute a mobile application, the communication device 113 is configured to communicate with the diaper sensor 120, and the camera device 114 is configured to capture a photograph, and the input/output device 115 allows a user (e.g., an infant's parent) to operate the mobile application.

In one embodiment, the server 150 is configured to store crowdsourcing data including a plurality of sensing criteria corresponding to a plurality of geographic regions (e.g., country, county and city), different genders (e.g., male and female), a plurality of ages (e.g., years), a plurality of diaper data (e.g., diaper brand/model).

The mobile device 110 is configured to execute the mobile application (e.g., a diaper APP) to pair with the diaper sensor 120. The user (e.g., an infant's parent) operates the mobile application, so that the mobile device 110 can transmit location information (e.g., GPS information, residence settings of community website, the retail country of the diaper sensor 120), a wearer's sex and age, and a brand or a model of a diaper to the server 150. The server 150 finds one geographic region corresponding to the location information from the geographic regions, one gender corresponding to the wearer's sex from the genders, and one diaper datum corresponding to the brand or model of the diaper from the diaper data, so as to select a corresponding sensing criterion from the sensing criteria and to return the corresponding sensing criterion to the mobile device 110. The mobile device 110 is based on the corresponding sensing criterion to determine whether a diaper sensing signal from the diaper sensor 120 reflect that the diaper 130 needs to be replaced.

Moreover, the sensing criteria in the crowdsourcing data correspond to relations among the geographical regions, the genders, the ages, the diaper data and a plurality of environmental parameters (e.g., environment temperature and humidity). Before the diaper 130 attached to the diaper sensor 120 is worn, the diaper sensor 120 senses an environmental sensing signal (e.g., environment temperature and humidity signals), so that the mobile device 110 sends transmit the location information, the wearer's sex and age, the brand or the model of diaper 130, and the environmental sensing signal to the server 150, so as to obtain the above-mentioned corresponding sensing criterion.

When the mobile device 110 is based on the corresponding sensing criterion to determine that the diaper sensing signal from the diaper sensor 120 reflect that the diaper 130 needs to be replaced, the mobile device 110 executes a prompt action of replacement of the diaper (e.g., shock, ringtones, screen tips), so as to prompt the user (e.g., an infant's parent) to change the diaper 130. After the mobile device 110 executes the prompt action of replacement of the diaper, the user can change the diaper 130 and input feedback information (e.g., too early to remind, too late to remind and so forth) through the mobile device 110. The mobile device 110 adjusts the corresponding sensing criterion based on the user feedback information and uploads the user feedback information to the server 150, so that the server 150 uses the user feedback information as a basis of updating the crowdsourcing data.

In one embodiment, the crowdsourcing data are compiled into a record database. The calibration data can be obtained from the sensor database for the judgment/evaluation. That is, the calibration data is obtained from the sensed data. Specifically, the server 150 can receive user feedback information of all parties (e.g., area, gender, age, diaper information, diaper changing time, etc.) through the crowd outsourcing technology and then collect the data into the crowdsourcing data.

In FIG. 1, the diaper sensor 120 includes a wireless transmission device 121, a temperature sensor 122, a humidity sensor 123 and a controller 124. The controller 124 is electrically connected to the wireless transmission device 121, the temperature sensor 122 and the humidity sensor 123.

In practice, the wireless transmission device 121 may include a Bluetooth module or other short-distance transmission module. The temperature sensor 122 may be an electronic component that converts temperature into electronic data. The humidity sensor 123 may be resistive and capacitive hygrometers. The controller 124 may be a microcontroller or other circuit.

In use, the temperature sensor 122 is configured to sense a temperature value. The humidity sensor 123 is configured to sense a humidity value. The controller 124 is configured to incorporate the temperature value and the humidity value into the diaper sensing signal so as to transmit the diaper sensing signal to the mobile device 110 through the wireless transmitter 121, so that the mobile device 110 determines whether the temperature value and the humidity value falls within a predetermined temperature range and a preset humidity range respectively. The mobile device determines that the diaper 130 which needs to be replaced when the temperature value and the humidity value falls within the predetermined temperature range and the preset humidity range respectively.

Figure 2:
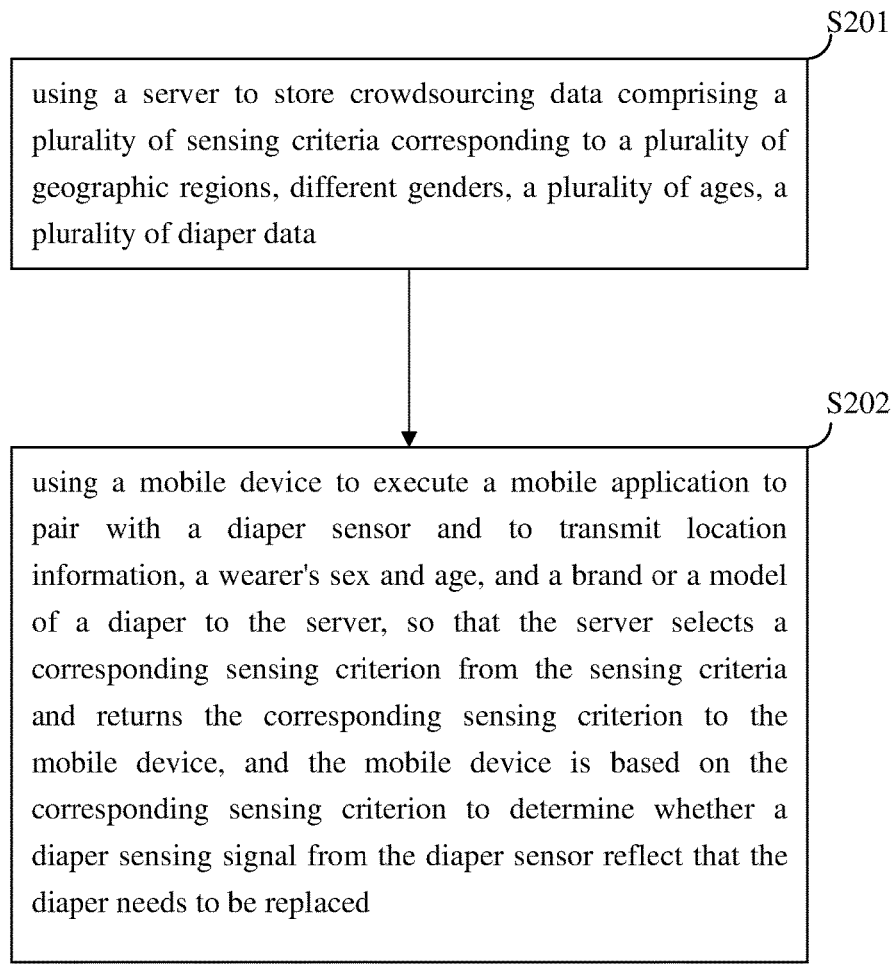
FIG. 2 is a flow chart of a diaper prediction and correction method according to some embodiments of the present disclosure.

For a more complete understanding of a diaper prediction and correction method performed by the diaper prediction and correction system 100, referring FIG. 2, FIG. 2 is a flow chart of the diaper prediction and correction method 200 according to an embodiment of the present invention. As shown in FIG. 2, the diaper care method 200 includes operations S201 and S202. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

In operation S201, a server 150 is used to store crowdsourcing data including a plurality of sensing criteria corresponding to a plurality of geographic regions, different genders, a plurality of ages, a plurality of diaper data.

In operation S202, a mobile device 110 is used to execute a mobile application to pair with a diaper sensor 120 and to transmit location information, a wearer's sex and age, and a brand or a model of a diaper to the server 150, so that the server 150 selects a corresponding sensing criterion from the sensing criteria and returns the corresponding sensing criterion to the mobile device 110, and the mobile device 110 is based on the corresponding sensing criterion to determine whether a diaper sensing signal from the diaper sensor reflect that the diaper needs to be replaced.

In one embodiment, the sensing criteria in the crowdsourcing data correspond to relations among the geographical regions, the genders, the ages, the diaper data and a plurality of environmental parameters. The operation S202 includes: before the diaper attached to the diaper sensor is worn, using the diaper sensor to sense an environmental sensing signal, so that the mobile device sends transmit the location information, the wearer's sex and age, the brand or the model of diaper, and the environmental sensing signal to the server, so as to obtain the corresponding sensing criterion.

In the diaper prediction and correction method 200, after the mobile device 110 executes a prompt action of replacement of the diaper, the mobile device 110 is used to receive user feedback information, adjust the corresponding sensing criterion based on the user feedback information and upload the user feedback information to the server 150, so that the server 150 uses the user feedback information as a basis of updating the crowdsourcing data.

In one embodiment, the operation S202 includes: using the diaper sensor 120 to incorporate a temperature value and a humidity value of the diaper 130 into the diaper sensing signal so as to transmit the diaper sensing signal to the mobile device 110, so that the mobile device 110 determines whether the temperature value and the humidity value falls within a predetermined temperature range and a preset humidity range respectively. The mobile device 110 determines that the diaper 130 which needs to be replaced when the temperature value and the humidity value falls within the predetermined temperature range and the preset humidity range respectively.

In view of above, the present invention provides a set of mechanisms for the diaper sensor to quickly and easily establish a "customized predictive model" for wearers of different diaper brands, different breathable degrees, and different ages, in both hot and cold environments, so as to accurately determine when to change diapers.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A diaper prediction and correction system, comprising:
   a diaper sensor;
   a server configured to store crowdsourcing data comprising a plurality of sensing criteria corresponding to a plurality of geographic regions, different genders, a plurality of ages, a plurality of diaper data; and
   a mobile device configured to execute a mobile application to pair with the diaper sensor and to transmit a location information, a wearer's sex and age, and a brand or a model of a diaper to the server, so that the server selects a corresponding sensing criterion from the sensing criteria and returns the corresponding sensing criterion to the mobile device, and the mobile device is based on the corresponding sensing criterion to determine whether a diaper sensing signal from the diaper sensor reflect that the diaper needs to be replaced.

2. The diaper prediction and correction system of claim 1, wherein the sensing criteria in the crowdsourcing data correspond to relations among the geographical regions, the genders, the ages, the diaper data and a plurality of environmental parameters, and before the diaper attached to the diaper sensor is worn, the diaper sensor senses an environmental sensing signal, so that the mobile device sends transmit the location information, the wearer's sex and age, the brand or the model of diaper, and the environmental sensing signal to the server, so as to obtain the corresponding sensing criterion.

3. The diaper prediction and correction system of claim 1, wherein after the mobile device executes a prompt action of replacement of the diaper, the mobile device receives user feedback information, adjusts the corresponding sensing criterion based on the user feedback information and uploads the user feedback information to the server, so that the server uses the user feedback information as a basis of updating the crowdsourcing data.

4. The diaper prediction and correction system of claim 1, wherein the diaper sensor comprises:
   a wireless transmitter;
   a temperature sensor configured to sense a temperature value;
   a humidity sensor configured to sense a humidity value; and
   a controller configured to incorporate the temperature value and the humidity value into the diaper sensing signal so as to transmit the diaper sensing signal to the mobile device through the wireless transmitter, so that the mobile device determines whether the temperature value and the humidity value falls within a predetermined temperature range and a preset humidity range respectively, and the mobile device determines that the diaper which needs to be replaced when the temperature value and the humidity value falls within the predetermined temperature range and the preset humidity range respectively.

5. A diaper prediction and correction method, comprising steps of:
   (A) using a server to store crowdsourcing data comprising a plurality of sensing criteria corresponding to a plurality of geographic regions, different genders, a plurality of ages, a plurality of diaper data; and
   (B) using a mobile device to execute a mobile application to pair with a diaper sensor and to transmit location information, a wearer's sex and age, and a brand or a model of a diaper to the server, so that the server selects a corresponding sensing criterion from the sensing criteria and returns the corresponding sensing criterion to the mobile device, and the mobile device is based on the corresponding sensing criterion to determine whether a diaper sensing signal from the diaper sensor reflect that the diaper needs to be replaced.

6. The diaper prediction and correction method of claim 5, wherein the sensing criteria in the crowdsourcing data correspond to relations among the geographical regions, the genders, the ages, the diaper data and a plurality of environmental parameters, and the step (B) further comprising:
   before the diaper attached to the diaper sensor is worn, using the diaper sensor to sense an environmental sensing signal, so that the mobile device sends transmit the location information, the wearer's sex and age, the brand or the model of diaper, and the environmental sensing signal to the server, so as to obtain the corresponding sensing criterion.

7. The diaper prediction and correction method of claim 5, further comprising:
   after the mobile device executes a prompt action of replacement of the diaper, using the mobile device to receive user feedback information, adjust the corresponding sensing criterion based on the user feedback information and upload the user feedback information to the server, so that the server uses the user feedback information as a basis of updating the crowdsourcing data.

8. The diaper prediction and correction method of claim 5, wherein the step (B) comprises:
   using the diaper sensor to incorporate a temperature value and a humidity value of the diaper into the diaper sensing signal so as to transmit the diaper sensing signal to the mobile device, so that the mobile device determines whether the temperature value and the humidity value falls within a predetermined temperature range and a preset humidity range respectively, and the mobile device determines that the diaper which needs to be replaced when the temperature value and the humidity value falls within the predetermined temperature range and the preset humidity range respectively.

* * * * *